United States Patent [19]

Erath

[11] Patent Number: 4,860,755

[45] Date of Patent: Aug. 29, 1989

[54] DIFFERENTIAL PRESSURE APPLANATION TONOMETER

[75] Inventor: Louis W. Erath, Abbeville, La.

[73] Assignee: Erath-Young Instrument Company, Inc., Abbeville, La.

[21] Appl. No.: 153,436

[22] Filed: Feb. 8, 1988

[51] Int. Cl.$^4$ .............................................. A61B 3/16
[52] U.S. Cl. ..................................... 128/645; 128/652
[58] Field of Search ................................ 128/645, 652

[56] References Cited

U.S. PATENT DOCUMENTS

| | | | |
|---|---|---|---|
| 2,708,928 | 5/1955 | Zenatti | 128/2.05 |
| 2,966,795 | 1/1961 | Smyth | 73/78 |
| 3,049,001 | 8/1962 | Mackay et al. | 73/80 |
| 3,070,087 | 12/1962 | Sittel | 128/2 |
| 3,184,960 | 5/1965 | Murr et al. | 73/80 |
| 3,376,735 | 4/1968 | Garber et al. | 128/645 |
| 3,390,572 | 7/1968 | Murr | 73/80 |
| 3,572,319 | 3/1971 | Bittner et al. | 128/2 |
| 4,766,904 | 8/1988 | Kozin et al. | 128/652 |

OTHER PUBLICATIONS

"Fast, Automatic Ocular Pressure Measurement Based on an Exact Theory", IRE Transactions on Medical Electronics, Mackay & Marg, Apr. 1960, pp. 61–67.
"Tonometry: the Informed Choice", Distributed by Optical Radiation Corp., Ophthalmic Products Div., 1300 Optical Drive, Azusa, CA 91702.

Primary Examiner—Max Hindenburg
Assistant Examiner—J. P. Lacyk
Attorney, Agent, or Firm—Arnold, White & Durkee

[57] ABSTRACT

An applanation tonometer for sensing the intraocular pressure of the eye. The tonometer includes coaxial inner and outer probes which are placed in contact with the eye. The difference in longitudinal forces applied by the eye to the inner and outer probes is measured and the intraocular pressure is determined therefrom. The total pressure applied to the eye by the tonometer is not measured as only the differential pressure on the two probes is needed. The tonometer may include a feedback mechanism to oppose relative longitudinal movement between the probes, thus improving the linearity, accuracy and stability of the instrument. The differential-pressure sensing circuitry includes a sample-and-hold circuit for receiving the measured result and supplying it to an indicating meter. The circuitry also includes compensating means for compensating for the force effects of gravity on the masses of the device. Finally, a level sensing circuit is used to indicate that a complete measurement has been made when a predetermined force has been applied to the eye by the outer probe.

14 Claims, 2 Drawing Sheets

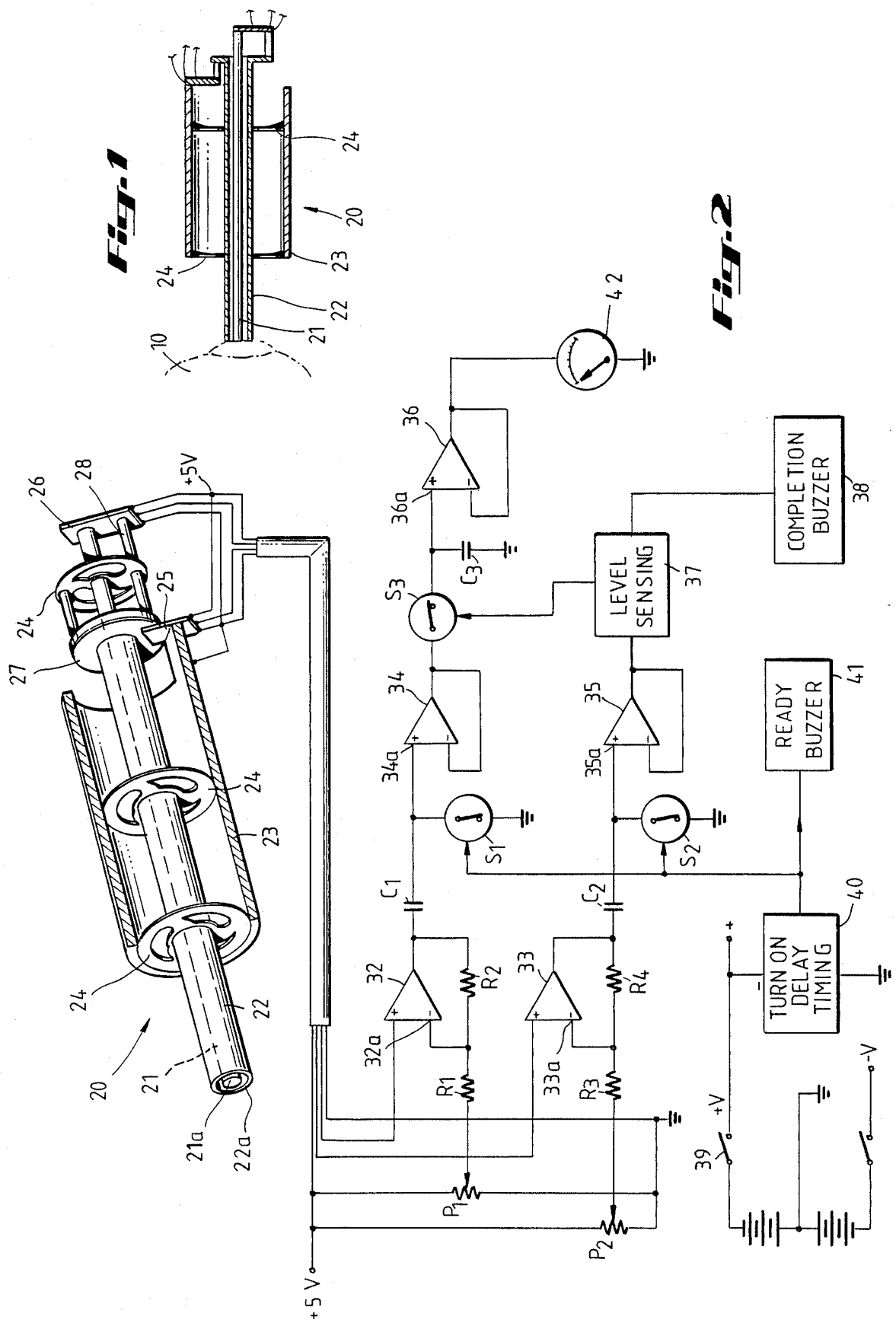

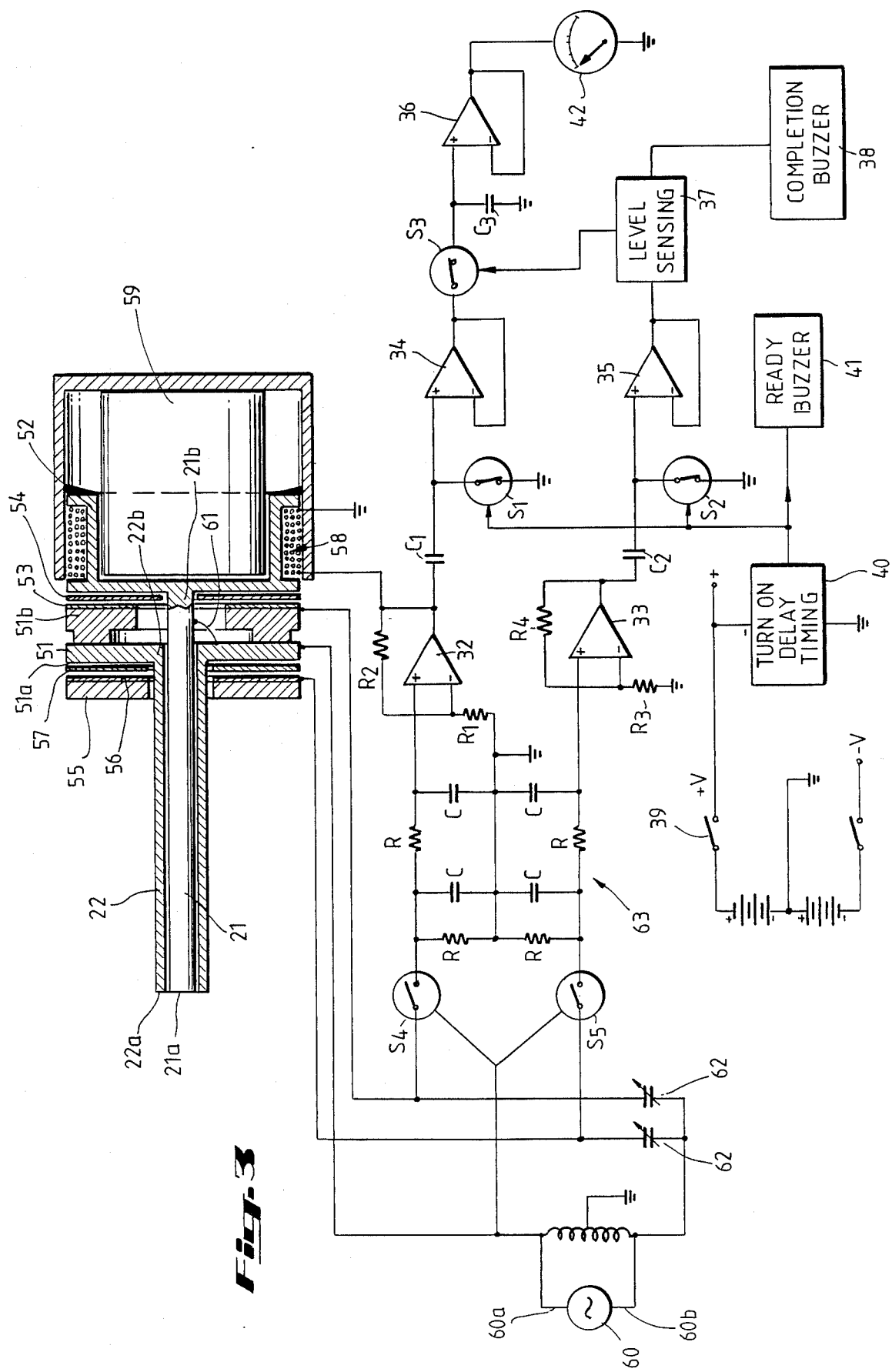

DIFFERENTIAL PRESSURE APPLANATION TONOMETER

FIELD OF THE INVENTION

The present invention relates to applanation tonometers which are used to measure the intraocular pressure of the eye. More specifically, the present invention relates to an applanation tonometer wherein a differential pressure between two probes is measured.

BACKGROUND OF THE INVENTION

Tonometry is the noninvasive measurement of the intraocular pressure of the eye and is commonly employed for the detection of glaucoma. The pressure within the healthy eye of a normal adult will typically be about 17 mm Hg (mercury). Glaucoma is a condition which results from an increase in the volume of fluid in the eye and usually manifests itself by an increase in intraocular pressure. Thus, measurement of this pressure is done to detect the onset of glaucoma.

Generally there are two types of tonometry: applanation and indentation. Applanation tonometry involves the flattening of a portion of the cornea while indentation tonometry involves indenting the cornea with some shape other than a flat surface. The human eye is made up of tissue and fluid which are mostly water. Because water is substantially incompressible, the pressure required to applanate or indent the cornea will be indicative of the intraocular pressure, assuming a normal ocular rigidity.

Several types of applanation tonometers have been developed and used over the years, including contact and non-contact devices. The contact-type devices generally attempt to measure the pressure within the eye by applying an external force which is then opposed by the pressure of the fluid in the eye. Schemes have been developed for transmitting pressure within the eye to some fluid or gas contained within the tonometer. An example of such a system is the Pneumatonometer in which an equilibrium between gas pressure and intraocular pressure across a thin membrane is sought. Other devices attempt to measure the pressure by allowing deflections in membranes or crystals when the device is pressed against the eye. The Mackay-Marg tonometer and the Computon microtonometer are examples of such devices.

Non-contact tonometry normally uses a stream of air to flatten a portion of the cornea while a light source is reflected off of that flattened portion. The force of the airstream required to flatten the cornea is indicative of the intraocular pressure.

Both contact and non-contact tonometers have many drawbacks. The most obvious drawbacks to the majority of the contact tonometers are the risk of damage to the eye and the reliability of the measurement obtained. The drawbacks to the non-contact tonometer are well known and include cost, the level of skill required for operation and the reliability of the measurement.

SUMMARY OF THE INVENTION

An applanation tonometer according to the present invention provides a safe, reliable measurement in a portable, cost-effective device. The tonometer includes coaxial inner and outer probes which are used to applanate the cornea. The difference in pressure exerted by the eye against the inner and outer probes is measured and is indicative of the intraocular pressure.

The coaxial probes are held in a housing and are longitudinally slidable in the housing. Sensors detect relative longitudinal movement between the probes and relative longitudinal movement between the outer probe and the housing. Alternatively, sensors detect the difference in longitudinal forces applied to the probes and difference in longitudinal forces applied to the outer probe and the housing. The differential movement or force between the outer probe and the housing is used only to limit the total pressure applied to the eye and to activate a sample-and-hold circuit when a complete measurement has been made. The differential movement or force between the two probes is a direct indication of the intraocular pressure. This differential movement or force between the two probes is unaffected by the total pressure applied to the eye.

A feedback mechanism is employed in one embodiment to oppose relative longitudinal movement between the probes. Also, compensating means are used to offset the force effects of gravity on the elements of the device.

BRIEF DESCRIPTION OF THE DRAWINGS

FIG. 1 is an illustration of how the probes of an applanation tonometer of the present invention are used to measure the intraocular pressure of the eye.

FIG. 2 shows a cutaway and the schematic for one embodiment of the present invention wherein solid state strain gauges are used to detect differences in pressures between the inner and outer probes and between the outer probe and the housing.

FIG. 3 shows the cross-section and schematic for another embodiment of the present invention wherein capacitors are used to sense differences in forces between the inner and outer probes and between the outer probe and the housing.

DETAILED DESCRIPTION OF THE PREFERRED EMBODIMENT

FIG. 1 is a section view illustrating how a tonometer according to the present invention contacts the eye to applanate, or flatten, a portion of the cornea. The eye 10 is an prolate spheroid which is made up of tissue and fluid which are high in water content. The normal eye has a hydrostatic intraocular pressure of approximately 17 mm Hg. Higher pressures than normal are symptomatic of the onset of glaucoma.

As is known in the art, the intraocular pressure can be sensed by applanating a portion of the cornea and measuring the force required to flatten a known area. At equilibrium, that force will be approximately equal to the pressure within the eye. One embodiment 20 of the present invention employs two probes 21 and 22, arranged coaxially, to press against the eye 10. The probes 21 and 22 are slidable longitudinally with respect to one another and together are slidably mounted in a housing 23. When the probes contact the eye, because of the shape of the eye, the inner probe 21 will actually contact the eye first and the outer probe 22 will contact the eye shortly thereafter. To flatten the cornea, a greater force will be exerted by the eye's hydrostatic pressure on the inner probe 21 than on the outer probe 22. As the device 20 is moved into full contact with the eye 10, the pressure difference between the inner and outer probes 21 and 22 will rise until the outer probe 22 contacts the eye, after which the pressure difference will plateau, or level off. This difference in force or pressure is sensed by the device 20 and correlates to the intraocular pressure of the eye. As will be seen, if the device 20 is further pressed to the eye 10 after the outer probe 22 has contacted the eye, the inner and outer probes, together, will slide in the housing 23 but the differential pressure between the probes 21 and 22 will not be increased.

Referring now to FIG. 2, one embodiment of the present invention is shown in a cutaway view, along with a schematic diagram of the associated circuitry. The tonometer 20 includes coaxial inner and outer probes, 21 and 22 respectively, whose first ends, 21a and 22a, lie substantially in a single plane perpendicular to the longitudinal axis of the probes. The outer probe 22 is a tube of about two-tenths (0.2) inch in diameter and is suspended in a generally cylindrical housing 23 by means of flat springs 24 attached to the probe 22 and the housing 23. Thus, limited longitudinal movement of the outer probe 22 in the housing 23 is provided. The inner probe 21 is suspended in the outer probe 22 also by means of flat springs (not shown), providing limited longitudinal movement of the inner probe 21 with respect to the outer probe 22.

Solid state strain gauges 25 and 26 are used to detect relative longitudinal movement between the outer probe 22 and the housing 23 and between the inner probe 21 and the outer probe 22, respectively. The strain gauge 25 may be attached to the outer probe 22 and the housing 23 in any suitable manner and, in the embodiment in FIG. 2, a washer-like disk 27 attached to the outer probe 22 provides a means for attaching the strain gauge 25. A spacer 28 attached to the disk 27 forms an extension of the outer probe 22 and the strain gauge 26 is mounted between the spacer 28 and an extension of the inner probe 21. Suitable strain gauges are made by Kulite Semiconductor Products, Inc. of Ridgefield, N.J. and are known as Model Number UHP 5000-60, but other gauges may be used with equal success.

A first bridge 31 is formed using the outer strain gauge 25 and a first potentiometer P2 with the output of the first bridge being applied to an operational amplifier 33. A second bridge 32 is formed using the inner strain gauge 26 and a second potentiometer P1 with the output of the second bridge being applied to an operational amplifier 32. Potentiometers P1 and P2 may be adjusted so as to calibrate the device 20. As can be seen in FIG. 2, resistors R1 and R3 are connected between the potentiometers P1 and P2 and the inverting inputs 32a and 33a of operational amplifiers 32 and 33, respectively. Resistors R3 and R4 are connected, respectively, between the outputs of op-amps 32 and 33 and their inverting inputs 32a and 33a. The gain of amplifier 32 is set by the ratio of R2 to R1 and the gain of amplifier 33 is set by the ratio of R4 to R3. The output of amplifier 32 represents the longitudinal displacement of the inner probe 21 with respect to the outer probe 22, or the difference in longitudinal forces applied to the probes 21 and 22.

The outputs of amplifiers 32 and 33 are connected to the non-inverting input terminals 34a and 35a of operational amplifiers 34 and 35, respectively, through capacitors C1 and C2. The input terminals 34a and 35a are also controllably connected to electrical ground through grounding switches S1 and S2. Capacitors C1 and C2 and switches S1 and S2 are used to compensate for gravitational effects on the probes 21 and 22 and for drift, as will be explained more fully below.

The output of amplifier 34 is connected, through a switch S3, to a first terminal of capacitor C3 and to the non-inverting input 36a of an operational amplifier 36. The second terminal of capacitor C3 is electrically grounded. The capacitor C3 and amplifier 36 form a sample-and-hold circuit, the operation of which will be described below. The output of amplifier 36 represents the difference in longitudinal pressures exerted on the inner and outer probes 21 and 22 and is connected to a meter 42 for visually displaying the magnitude of that pressure differential. The meter 42 is calibrated in mm of Hg and represents the intraocular pressure of the eye.

The output of operational amplifier 35 represents the difference in longitudinal pressures exerted on the outer probe 22 and the housing 23. This output provides an input to a level sensor 37 which may be controllably set to generate an electrical output signal when its input reaches a predetermined maximum. Such a device is made by Analog Devices and is known as a Model AD382. When the predetermined maximum pressure differential between the outer probe 22 and the housing 23 is reached, the level sensor 37 causes an output signal to be sent to the switch S3, causing it to open. A second output from level sensor 37 is sent to a buzzer 38 for generating an audible signal, signifying that the measurement is complete.

A switch 39 is used to power up the device 20 and its associated circuitry. The closing of switch 39 causes a five-volt (5V) supply to be connected to the bridges 31 and 32 and to a time delay device 40. A 2N556 device has been used as timing device 40 with success, although other suitable timers may be used. The timer 40 generates an output signal a preselected time after the closing of switch 39 and its output signal is connected to switches S1 and S2 and to a buzzer 41. The timer output signal causes the switches S1 and S2, which are normally-closed switches, to open and remain open until the switch 39 is opened. When switch 39 opens, switches S1 and S2 return to their closed positions. The output signal of the timer 40 also causes the buzzer 41 to generate an audible signal, indicating that the device 20 is ready for use.

The switches S1, S2 and S3 may be electronic switches such as Model CD4053 made by RCA, or may be other suitable devices which respond to an input signal by opening. The operational amplifiers 32, 33, 34, 35 and 36 may be Model TL084 by Texas Instruments or similar. These devices typically exhibit high input impedance.

The structure of the device having been described, its operation is as follows:

The device 20 is oriented in the position in which it will be used (i.e., horizontally or vertically) and the switch 39 is closed. Because the switches S1 and S2 are closed, capacitors C1 and C2 are grounded on one side and connected to receive outputs from amplifiers 32 and 33, respectively, on their other sides. The device 20 has not yet been placed in contact with the eye and the outputs from amplifiers 32 and 33 represent the effect of gravity on the inner probe 21 relative to the outer probe 22 and the effect of gravity on the outer probe 22 relative to the housing 23, respectively. Those "gravity effect outputs" are stored in the form of electrical charges on the capacitors C1 and C2. Also during the initial seconds after the closing of switch 39, electrical drifts and surges are allowed to stabilize.

When the time delay device 40 times out, it sends a signal to switches S1 and S2, causing them to open, and to the buzzer 41, causing it to indicate audibly that the device 20 is ready for use. When the switches S1 and S2 open, the charges on the capacitors C1 and C2 alter the outputs from amplifiers 32 and 33 before they are input to amplifiers 34 and 35. This alteration offsets the gravitational effects on the device parts and causes the inputs to amplifiers 34 and 35 to reflect only the forces resulting from contact between the device 20 and the eye.

When the buzzer 41 indicates that the tonometer 20 is ready for use, the operator touches the eye lightly with the probes 21 and 22. Because of the spherical configuration of the eye, the inner probe 21 contacts the eye first and the outer probe 22 contacts the eye shortly thereafter. When the inner probe 21 contacts the eye, it begins to slide longitudinally with respect to the outer probe 22. Strain gauge 26 senses the relative movement and a signal is input to the operational amplifier 32 which is proportional to that movement.

The deflection of the inner probe 21 with respect to the outer probe 22 continues until the outer probe 22 contacts the eye. At that point, the deflection of the inner probe 21 will be its greatest and the signal input to the amplifier 32 will be at its maximum level. Continued movement of the probes 21 and 22 toward the eye will result in deflection of the outer probe 22 with respect to the housing 23 but the inner probe 21 will remain stationary with respect to the outer probe 22. The deflection of the outer probe 22 with respect to the housing 23 will be sensed by the strain gauge 25 and a signal will be input to the operational amplifier 33 which is proportional to that deflection.

The output of amplifier 32 will represent the difference in pressures applied to the inner and outer probes 21 and 22, including any gravitational effects. The input to amplifier 34 will represent the difference in pressures applied to the probes 21 and 22, not including the gravitational effects, the effects of gravity having been offset, or compensated for, by the capacitor C1.

The output from amplifier 34 is connected through the normally-closed switch S3 to the sample-and-hold circuit including the capacitor C3 and the operational amplifier 36. The output from the amplifier 34 is stored on the capacitor C3 and is amplified by the amplifier 36 to drive the meter 42.

The output from amplifier 33 will represent the difference in pressures applied to the outer probe 22 and the housing 23, including any effects of gravity on the outer probe 22. The input to the operational amplifier 35 will represent the difference in pressures applied to the probe 22 and the housing 23, not including the gravitational effects, the effects of gravity having been offset, or compensated for, by the capacitor C2.

The output from amplifier 35 is the input to the level sensor 37. The sensor 37 is set to generate an output when its input reaches a pre-set maximum. Thus, when the outer probe 22 has moved a predetermined amount with respect to the housing 23, the sensor 37 is caused to generate output signals to the switch S3 and to the buzzer 38. The switch S3 is caused to open and the maximum output from amplifier 34 is stored on the capacitor C3. The buzzer 38 generates an audible signal, indicating that the measurement is complete. The output of the level sensor 37 to the switch S3 is a latched output which remains high until switch 39 is opened. Thus, switch S3 remains open and the meter 42 displays the intraocular pressure until the switch 39 is opened.

When switch 39 is opened, switches S1, S2 and S3 all resume their closed positions and the tonometer 20 is ready for another measurement.

A second embodiment of the present invention is illustrated in FIG. 3. The amplification, time delay, sample-and-hold and level sensing portions of the device of FIG. 3 are essentially identical to the corresponding portions of the device of FIG. 2 and those parts will not be explained again in detail.

The tonometer 20 of FIG. 3 includes inner and outer probes 21 and 22 which are coaxially arranged in a cylindrical housing (not shown) as before. As in the device of FIG. 2, the probes 21 and 22 may be suspended in place by means of flat springs or other suitable means.

Referring to FIG. 3, the outer probe 22 is generally cylindrical, being adapted at a first end 22a to contact the eye and terminating at its second end 22b in a first flange 51. The flange 51 has an inner diameter equal to the inside diameter of the probe 22 and an outside diameter larger than the outside diameter of the probe 22. Thus, opposing sides 51a and 51b are formed on the flange 51.

The inner probe 21 is generally rod-like in shape and extends through the outer probe 22 and coaxial with the probe 22. The inner probe 21 extends from a first end 21a, which is suitable for contacting the eye, to a second end 21b, which protrudes from the end 22b of the probe 22 and the flange 51. The ends 21a and 22a lie generally in a single plane perpendicular to the longitudinal axis of the probes 21 and 22.

The end 21b of the probe 21 terminates in a spool 52 which is generally cylindrical in shape. The outer diameter of the spool 52 is approximately equal to the outer diameter of the flange 51 and the spool 52 is spaced longitudinally from the flange 51. A space is formed between the spool 52 and the side 51b of the flange 51. An inner probe capacitor plate 53 is etched from copper-clad fiberglass board and is attached to the side 51b of the flange 51. A mica disk 54 is placed between the inner probe capacitor plate 53 and the spool 52 and is slightly compressed between the two. Thus, an inner probe capacitance is formed by the spool 52, the mica disk 54 and the inner probe capacitor plate 53.

A second annular flange 55 is positioned in the housing, attached to the inner wall of the housing, and is spaced longitudinally from the first flange 51. An outer probe capacitor plate 56 is etched from copper-clad fiberglass board and is attached to the second flange 55 so as to face the side 51a of the first flange 51. A second mica disk 57 is placed between the outer probe capacitor plate 56 and the flange 51 and is slightly compressed between the two. Thus, an outer probe capacitor is formed by the first flange 51, the mica disk 57 and the outer probe capacitor plate 56.

An electrical coil 58 is wound about the outer circumference of the spool 52. A magnet 59 having a diameter slightly less than the inner diameter of the spool 52 is inserted into the spool 52.

As shown in FIG. 3, the first flange 51 is connected to a first terminal 60a of a high-frequency voltage source 60 and the inner probe 21 is electrically connected to the outer probe 22 by means of a pigtail connection 61 or other suitable means. The second terminal 60b of the source 60 is connected to the inner and outer probe capacitor plates 53 and 56, respectively, through balancing capacitors 62. Thus, the inner probe capacitance and one balancing capacitor 62 are in electrical parallel with the outer probe capacitance and the second balancing capacitor 62. The balancing capacitors 62 are adjusted to equal the inner and outer probe capacitances or otherwise adjust the inputs to the synchronous switches S4 and S5 such that normally no signal appears at the terminals of the switches S4 and S5.

When pressure is applied axially to the inner probe 21, the inner probe capacitance decreases and the balance which had been obtained by the balancing capacitor 62 is altered so as to produce a signal at the synchronous switch S4. Likewise, when pressure is applied axially to the outer probe 22, the outer probe capacitance decreases and the balance which had been obtained by the balancing capacitor 62 is altered so as to produce a signal at the synchronous switch S5. The decrease in inner probe capacitance reflects a difference in pressures applied axially to the inner and outer probes 21 and 22, as in the case of the strain gauge 26 in the embodiment of FIG. 2. The decrease in outer probe capacitance reflects a difference in pressures applied axially to the outer probe 22 and the housing 23, as in the case of the strain gauge 25 in the embodiment of FIG. 2.

When the inner probe capacitance decreases because of a difference in axial pressures applied to the inner and outer probes 21 and 22, a high-frequency signal appears at the synchronous switch S4. The switch S4 is driven by the oscillator 60 and acts as a synchronous rectifier. It changes the AC off-balance signal to a pulsating DC signal which is smoothed by the R-C filter 63. The smoothed DC signal, representing the axial differential pressure applied to the inner and outer probes 21 and 22, is applied to the non-inverting input of the operational amplifier 32. The inverting input of the amplifier 32 is connected to electrical ground through resistor R1 and also receives feedback from the amplifier 32 output through resistor R2.

The output of amplifier 32 represents the pressure differential seen by the inner and outer probes 21 and 22, including gravitational effects, and is utilized in the same manner as the output from the amplifier 32 in the embodiment of FIG. 2. The amplifier 32 output is also connected to the coil 58 on the spool 52. The coil 58 is wound such that an electric current flowing in the coil creates a magnetic field which interacts with the field of the magnet 59 to exert a force which attempts to balance the pressure differential seen by the inner probe. That is, a difference in axial pressures between the inner and outer probes 21 and 22 results in a signal which is then fed back to the coil 58 to produce an axial force on the inner probe 21 to oppose motion due to the differential pressure between the inner and outer probes 21 and 22. This negative feedback arrangement improves the linearity, accuracy and stability of the tonometer 20.

When an axial pressure is applied to the outer probe 22, the inner and outer probes 21, the first flange 51 and the spool 52 all move together so that the inner probe capacitance is not affected. The outer probe capacitance will decrease as the axial pressure is applied to the outer probe 22 and an AC signal will appear at the synchronous switch S5. The switch S5, like the switch S4, acts as a synchronous rectifier and the signal received by it will be changed to a pulsating DC signal which is smoothed by the R-C filter 63. This smoothed DC signal represents the difference in axial pressures seen by the outer probe 22 and the housing 23 and is applied to the non-inverting input of the operational amplifier 33. The inverting input of the amplifier 33 is connected to electrical ground through resistor R3 and receives feedback from its output through resistor R4. The output from amplifier 33 represents the difference in axial pressures seen by the outer probe 22 and the housing 23 and is utilized in the same manner as the output from amplifier 33 in the embodiment of FIG. 2.

The feedback mechanism using coil 58 is unique in that the entire probe system is allowed to move without a force being generated by the coil and magnet. This is because the current in the coil is affected only by the differential sensor-amplifier system.

The capacitor sensor system provides many advantages. The mica (or other suitable dielectric) disk is mounted between the capacitor pates and the space between the plates is set at the thickness of the mica. This allows the probe to move in one direction only. This arrangement provides very high sensitivity because when the plates are pushed apart, air which has a dielectric constant of one causes the average dielectric constant to decrease rapidly, adding to the decrease in capacity due to the plates being moved apart.

It will now be appreciated by those of ordinary skill in the art that a new and useful tonometer has been shown. Although the invention has been described in terms of two specific embodiments, variations in those embodiments or other different embodiments may be used without departing from the principles of the present invention. The scope of the invention should therefore be limited only by the scope of the appended claims.

What is claimed is:

1. An applanation tonometer, comprising:
   first and second probes for contacting the surface of an eye, the probes being arranged coaxially in a housing and being movable longitudinally with respect to one another and with respect to the housing; and
   a first sensor circuit coupled to the first and second probes and operative to sense longitudinal movement of the first probe relative to the second probe and generate a first signal in response to the relative movement,
   the first signal being related to the intraocular pressure of the eye.

2. The applanation tonometer of claim 1, further comprising:
   a compensator coupled to the first and second probes and to the first sensor circuit, the compensator being operative to alter the first signal to compensate for gravity effects on the probes.

3. The tonometer of claim 2, wherein
   the compensator includes a first capacitor and a first grounding switch operatively connected to the first sensor circuit.

4. The tonometer of claim 3, further comprising a timer for opening the first grounding switch after a predetermined time after application of power to the first sensor circuit.

5. The tonometer of claim 4, further comprising an indicator coupled to receive the signal generated by the first sensor circuit, the indicator indicating a value representative of the intraocular pressure of the eye.

6. The tonometer of claim 1, further comprising a second sensor circuit coupled to the second probe and to the housing and operative to sense longitudinal movement of the second probe relative to the housing, the second sensor circuit generating a second signal in response thereto.

7. The tonometer of claim 6, wherein the second sensor circuit includes a level sensor coupled to receive the second signal, the level sensor being set to generate a limit signal in response to receiving the second signal having a pre-selected maximum value.

8. The tonometer of claim 7, further comprising a holding circuit coupled to the first sensor circuit, the holding operative to receive and hold the first signal and to provide an output signal proportional to the first signal, the holding circuit being coupled to the first sensor circuit through a switch, the switch being operative to receive the limit signal and to open in response thereto.

9. An application tonometer, comprising:
inner and outer probes for contacting the surface of an eye, the probes being arranged coaxially in a housing;
first sensing circuit means for sensing a difference in longitudinal forces applied to the inner and outer probes when the probes are placed in contact with the eye and for generating a signal proportional to the difference;
feedback means for receiving the signal and for applying an opposing longitudinal force to oppose movement of the inner probe relative to the outer probe,
the magnitude of the opposing longitudinal force being proportional to the magnitude of the signal, and
the magnitude of the signal being proportional to the intraocular pressure of the eye.

10. The tonometer of claim 9 wherein the signal generated by the first sensing circuit means is an electrical signal, and wherein the feedback means comprises:
a magnet for creating a first magnetic field; and
an electrical coil adjacent the magnet, the coil adapted to receive the electrical signal and create a second magnetic field,
the second magnetic field opposing the first magnetic field to create the opposing longitudinal force.

11. The tonometer of claim 10, wherein the first sensing circuit means includes:
an inner probe capacitor formed between the inner and outer probes, the capacitance of the capacitor being variable in response to a difference in longitudinal forces applied to the inner and outer probes; and
a first amplifier circuit means for detecting a variation in the capacitance of the inner probe capacitor and for generating a first electrical signal in response thereto, the magnitude of the first electrical signal being proportional to the variation in the capacitance.

12. The tonometer of claim 11, further comprising a second sensing circuit having:
an outer probe formed between the outer probe and the housing, the capacitance of the outer probe capacitor being variable in response to a difference in longitudinal forces applied to the outer probe and to the housing;
a second amplifier circuit means for detecting a variation in the capacitance of the outer probe capacitor and for generating a second electrical signal in response thereto, the magnitude of the second electrical signal being proportional to the variation in the capacitance; and
a level sensor means for receiving the second electrical signal and generating an output signal when the second electrical signal reaches a pre-selected maximum.

13. The tonometer of claim 12, further including an output circuit having a switch coupling the first electrical signal to a holding capacitor and an indicator circuit, the switch adapted to receive the output signal from the level sensor means and responsive to open to isolate the holding capacitor and indicator circuit from the first sensing circuit means.

14. A differential applanation tonometer, comprising:
an outer cylindrical probe adapted at a first end to contact the surface of an eye and having, at a second end, a first flange about its outer circumference;
an inner rod-like probe coaxial with and positioned within the outer probe, the inner probe being adapted at a first end to contact the surface of an eye, the first ends of the inner and outer probes lying substantially in a plan perpendicular to their longitudinal axes;
a cylindrical spool connected to a second end of the inner probe and being spaced longitudinally from the first flange, the spool having an outer diameter substantially equal to the outer diameter of the first flange;
an electrical winding about the outer circumference of the spool;
a magnet for location adjacent the spool;
a generally cylindrical housing for receiving the inner and outer probes, the spool and the magnet, the probes and spool being slidable longitudinally within the housing;
a second flange positioned about the circumference of the housing and spaced longitudinally from the first flange on the outer probe;
an outer probe capacitance formed between the first and second flanges;
an inner probe capacitance formed between the first flange and one end of the spool;
a first sensing circuit connected to the inner probe capacitance and operative to sense variations in the inner probe capacitance;
a second sensing circuit connected to the outer probe capacitance and operative to sense variations in the outer probe capacitance;
a compensator connected to the first and second sensing circuits and operative to compensate for gravity force effects on the outer and inner probes;
a level sensor operative to sense a predetermined level of force differential between the outer probe and the housing and responsive to generate a signal;
the electrical winding adapted to receive a signal from the first sensing circuit and operative to coact with the magnet to apply a longitudinal force to the inner probe to oppose longitudinal movement by the inner probe to the outer probe.

* * * * *

UNITED STATES PATENT AND TRADEMARK OFFICE
CERTIFICATE OF CORRECTION

PATENT NO. : 4,860,755

DATED : August 29, 1989

INVENTOR(S) : Louis W. Erath

It is certified that error appears in the above—identified patent and that said Letters Patent is hereby corrected as shown below:

Column 10, line 38: insert "inner" before circumference.

Column 10, line 62: insert "relative" before to the.

Signed and Sealed this

Sixth Day of November, 1990

Attest:

HARRY F. MANBECK, JR.

*Attesting Officer*  *Commissioner of Patents and Trademarks*